(12) United States Patent
Sarkela et al.

(10) Patent No.: US 10,780,239 B2
(45) Date of Patent: Sep. 22, 2020

(54) METHOD AND SYSTEM FOR CONTROLLING PATIENT SEDATION AND SPONTANEOUS BREATHING INTENSITY

(71) Applicant: General Electric Company, Schenectady, NY (US)

(72) Inventors: Mika Olli Kristian Sarkela, Helsinki (FI); Erkki Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 309 days.

(21) Appl. No.: 15/988,951

(22) Filed: May 24, 2018

(65) Prior Publication Data

US 2019/0358418 A1   Nov. 28, 2019

(51) Int. Cl.
*A61M 16/00* (2006.01)
*A61M 16/10* (2006.01)
(Continued)

(52) U.S. Cl.
CPC .... *A61M 16/0069* (2014.02); *A61M 16/0081* (2014.02); *A61M 16/026* (2017.08);
(Continued)

(58) Field of Classification Search
CPC ....... A61M 16/009–0093; A61M 16/021–024; A61M 16/06;
(Continued)

(56) References Cited

U.S. PATENT DOCUMENTS 5,237,990 A * 8/1993 Psaros .................. A61M 16/18
128/203.12

6,131,571 A   10/2000 Lampotang et al.
(Continued)

FOREIGN PATENT DOCUMENTS

| WO | 2008091789 A1 | 7/2008 |
| WO | 2009123981 A1 | 10/2009 |
| WO | 2013098717 A1 | 7/2013 |

OTHER PUBLICATIONS

Holk et al., "Continuous non-invasive monitoring of energy expenditure, oxygen consumption and alveolar ventilation during controlled ventilation: validation in an oxygen lung model", Acta Anaesthesiol Scand. 1996, 40; 530-537.
(Continued)

*Primary Examiner* — Rachel T Sippel
*Assistant Examiner* — Benjamin M. Kusiak
(74) *Attorney, Agent, or Firm* — Andrus Intellectual Property Law, LLP

(57) ABSTRACT

A system for controlling patient sedation and spontaneous breathing intensity includes a ventilator system that delivers ventilation to the patient. The system further includes a spontaneous breathing control module configured to determine a first spontaneous breathing intensity at a first sedative status of the patient, and a second spontaneous breathing intensity at a second sedative status of the patient. A sedation/breathing relationship is then defined between spontaneous breathing intensity and sedative status for the patient based on the first and second sedative statuses and the first and second spontaneous breathing intensities. The spontaneous breathing control module then receives a desired spontaneous breathing intensity for the patient and determines a desired sedative status that achieves that desired spontaneous breathing intensity based on the sedation/breathing relationship.

23 Claims, 6 Drawing Sheets

(51) Int. Cl.
A61B 5/04 (2006.01)
A61B 5/00 (2006.01)

(52) U.S. Cl.
CPC ....... *A61M 16/104* (2013.01); *A61B 5/04004* (2013.01); *A61B 5/4821* (2013.01); *A61M 16/1015* (2014.02); *A61M 2016/0042* (2013.01); *A61M 2202/0241* (2013.01); *A61M 2230/202* (2013.01); *A61M 2230/205* (2013.01); *A61M 2230/208* (2013.01); *A61M 2230/42* (2013.01)

(58) Field of Classification Search
CPC ........... A61M 16/0816; A61M 16/0833–0858; A61M 16/104; A61M 16/12; A61M 2016/0015–0042; A61M 2016/102–1035
USPC ............ 128/200.24, 203.12–203.14, 203.25, 128/204.21–204.23
See application file for complete search history.

(56) References Cited

U.S. PATENT DOCUMENTS

| | | | |
|---|---|---|---|
| 7,334,578 B2 | 2/2008 | Biondi et al. | |
| 8,789,529 B2* | 7/2014 | Vandine | A61M 16/0051 128/204.23 |
| 2004/0249300 A1 | 12/2004 | Miller | |
| 2007/0163590 A1 | 7/2007 | Bassin | |
| 2008/0236582 A1 | 10/2008 | Tehrani | |
| 2009/0188502 A1 | 7/2009 | Tiedje | |
| 2010/0236555 A1 | 9/2010 | Jafari et al. | |
| 2011/0108034 A1 | 5/2011 | Vietio-Oja | |
| 2011/0232641 A1* | 9/2011 | Haggblom | A61M 16/205 128/204.21 |
| 2011/0301436 A1 | 12/2011 | Teixeira | |
| 2012/0000470 A1 | 1/2012 | Hensley et al. | |
| 2012/0216811 A1* | 8/2012 | Kimm | A61M 16/024 128/204.23 |
| 2013/0047989 A1 | 2/2013 | Vandine et al. | |
| 2014/0060540 A1* | 3/2014 | Milne | A61B 5/0205 128/204.23 |
| 2015/0114395 A1 | 4/2015 | Heinonen et al. | |
| 2016/0310690 A1* | 10/2016 | Summers | A61M 39/26 |
| 2018/0093063 A1* | 4/2018 | Rajan | A61M 16/0045 |
| 2018/0280641 A1* | 10/2018 | White | A61M 16/024 |

OTHER PUBLICATIONS

Laubscher et al., "An Adaptive Lung Ventilation Controller", IEEE 1994 (0018-9294).
Laubscher et al., "The automatic selection of ventilation parameters during the initial phase of mechanical ventilation", Intesive Care Med (1996) 22: 199-207.
Westenskow et al., "A Microprocessor Based Feedback Controller for Mechanical Ventilation", Annals of Biomedical Engineering, vol. 10, pp. 35-48, 1982.
Drager, "Smart Ventilation Control (SVC)", 2016 Dragerwerk AG & Co. KGaA.
Drager, "Protective Ventilation in the OR", 2016 Drägerwerk AG & Co. KGaA.
Guarracino et al., "Target controlled infusion: TCI", Minerva Anestesiol. 2005, vol. 71, N. 6; 335-337.

* cited by examiner

METHOD AND SYSTEM FOR CONTROLLING PATIENT SEDATION AND SPONTANEOUS BREATHING INTENSITY

BACKGROUND

The disclosure generally relates to methods and systems for assessing and controlling patient sedation, and more specifically to controlling the level of patient sedation to achieve a requested intensity of a patient's spontaneous breathing action response during ventilator applied breathing support, and in addition for assessing a readiness of a patient to be weaned from a ventilator.

Electroencephalography (EEG) is a well-established method for assessing brain activity. When measurement electrodes are attached on the skin of the skull surface, the weak biopotential signals generated in the pyramid cells of the cortex may be recorded and analyzed. The EEG has been in wide use for decades in basic research of the neural systems of the brain as well as in the clinical diagnosis of various central nervous system diseases and disorders.

Electromyography (EMG) is a method for recording electrical biopotentials of muscles. In a surface EMG measurement, the electrodes are attached onto the surface of the skin overlying a muscle. When a biopotential signal is recorded from the forehead of a subject, the recorded signal indicates both the activity of the facial muscles (fEMG) and the brain (EEG).

Drug that are used to decrease level of consciousness and produce sleepiness of intensive care patient are, for example, Propofol, Midazolam and Dexmedetomidine. All of the above-mentioned drugs affect directly to either GABAergic or $alfa_2$-adrenergic receptors of the brain. Therefore, EEG is the state-of-the-art measurement for the drug effect, or sedation level, determination of these sedative drugs. Opioids, like Fentanyl, are also commonly used for sedative purposes. Opioids act by binding to opioid receptors, which are located both in the parts of peripheral and central nervous system, and also in the brain. Opioid drug effect can also be seen on the EEG signal, although with typical clinical doses the effect is not so prominent as, for example, with Propofol.

Entropy™ of GE Healthcare is one of the commercially available devices that automatically process and derives the EEG and fEMG signal for objective quantification of the drug effect. Entropy produces two indices; State Entropy (SE) is derived from the frequency range of 0.8-32 Hz and it mostly quantifies neuronal activity of the brain cortex, whereas Response Entropy (RE) is derived from the frequency range of 0.8-47 Hz and it contains larger amount of facial muscle activity. Other well-known devices for the same purpose are Bispectral Index™ (BIS™) of Medtronic and Patient State Index (PSi™) of Masimo, for example.

The above-mentioned indices are mainly based on the EEG signal, even though they are affected by the fEMG signal if facial muscles are active. Indices based mostly on the fEMG signal are also presented. Facial muscles of frontal area are innervated by seventh cranial nerve that emerges from the brainstem, therefore facial muscle activity of sedated patient could be used to monitor sedative drug effect. One potential method for the purpose is the Responsiveness Index (Lapinlampi et al., The Canadian Journal of Neurological Sciences, 2014; 41; 611-619).

Ventilation support is needed when a patient cannot meet the gas exchange demand with his own respiratory action. Such situations take place typically during intensive care and surgical anesthesia. Typical reasons for inability to maintain the gas exchange demand may be sedation, muscle relaxation and muscular weakening due to underlying disease and long inactivity. The ventilation support is used to enhance carbon dioxide ($CO_2$) clearance and oxygen delivery to the patient. Ventilation can also be used for the delivery of gaseous anesthetic agents.

Ventilation support is divided into two categories: full mechanical ventilation and spontaneous breathing support, or pressure support. In mechanical ventilation, the ventilator dictates the breath rate and volume. This is necessary when, for example, muscle relaxants are administered. By contrast, in spontaneous breathing support the patient maintains the respiratory rhythm and the ventilator is controlled to detect inspiration breaths. In spontaneous support ventilation, the ventilator adds inspiration pressure as a response to patient generated spontaneous breath.

Weaning the patients from artificial ventilation is central goal in intensive care ventilation. Problems in weaning increase with the amount of time that patient spent on the full mechanical ventilation. During the stay patients often develop ventilator dependency, and ability to maintain breathing on their own degrades. This dependency may prolong the stay on ventilator therapy even though the patient is already recovered from the primary illness. Prolonged ventilation increases risk for lung inflammation known as ventilator induced lung injury (VILI). Even worse, inflammatory mediator may spread from the lungs to other organs developing multiple-organ-failure. Mortality of such patients is high, and thus, minimizing the amount of time that a patient remains as the stay on ventilator is a primary goal for intensive care.

SUMMARY

The present disclosure relates to a system for controlling patient sedation and spontaneous breathing intensity. The system includes a ventilator system that delivers ventilation to the patient. The system further includes a spontaneous breathing control module configured to determine a first spontaneous breathing intensity at a first sedative status of the patient, and a second spontaneous breathing intensity at a second sedative status of the patient. A sedation/breathing relationship is then defined between spontaneous breathing intensity and sedative status for the patient based on the first and second sedative statuses and the first and second spontaneous breathing intensities. The spontaneous breathing control module then receives a desired spontaneous breathing intensity for the patient and determines a desired sedative status that achieves the desired spontaneous breathing intensity based on the sedation/breathing relationship.

In one embodiment, a system for controlling patient sedation and spontaneous breathing intensity includes a ventilator system that delivers ventilation to the patient. The system further includes a spontaneous breathing control module configured to determine a first spontaneous breathing intensity at a first sedative status of the patient, and a second spontaneous breathing intensity at a second sedative status of the patient. A sedation/breathing relationship is then defined between spontaneous breathing intensity and sedative status for the patient based on the first and second sedative statuses and the first and second spontaneous breathing intensities. The spontaneous breathing control module then receives a desired spontaneous breathing intensity for the patient and determines a desired sedative status that achieves that desired spontaneous breathing intensity based on the sedation/breathing relationship.

In one embodiment, a method of controlling sedation and spontaneous breathing intensity of a patient includes determining a first spontaneous breathing intensity at a first sedative status of the patient. A second spontaneous breathing intensity is determined at a second sedative status of the patient. A sedation/breathing relationship between spontaneous breathing intensity and sedative status is defined for the patient based on the first and second sedative statuses and the first and second spontaneous breathing intensities. The sedation/breathing relationship is then used to determine a desired sedative status that achieves a desired spontaneous breathing intensity in the patient. One or more drug delivery devices may then be controlled to deliver the desired sedative status to the patient so as to achieve the desired spontaneous breathing intensity in the patient.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

The leading hypothesis for weaning problems is respiratory muscle atrophy that develops rapidly in the unused muscles during mechanical ventilation. As preventative treatment, the inventors have recognized that pressure support ventilation triggered by the patient's spontaneous inspiration action is effective in maintaining the respiratory muscle strength. Thus, support of patient generated spontaneous breathing with added ventilation pressure is a preferred ventilation method for a patient in intensive care, and increasingly during anesthesia whenever the surgery does not require complete relaxation. The rationale for its use is to maintain the patient's muscular activity and ease the weaning from ventilation. However, excessive demand for patient inspiration action, either in duration or intensity, may result in patient fatigue, and should thus be avoided.

Present systems for spontaneous breathing support operate such that the clinician controls the amount of ventilation to maintain appropriate $CO_2$ concentration or partial pressure for the patient. This level can be determined by analysis of blood sample for arterial blood $CO_2$ partial pressure, $PaCO_2$. However, because this is a discrete measurement, end-expiratory gas $CO_2$ ($EtCO_2$) concentration is often used as surrogate for this. A typical $EtCO_2$ value is around 5%-6%, or 5-6 kPa, but in certain circumstances the optimum value for a particular patient may deviate from this. Similarly, patient metabolic $CO_2$ production varies between patients. This depends, for example, on patient size, age, gender, anxiety level, sedation, etc. Further, some treatment actions can impact a patient's $CO_2$ level.

Figure 2:
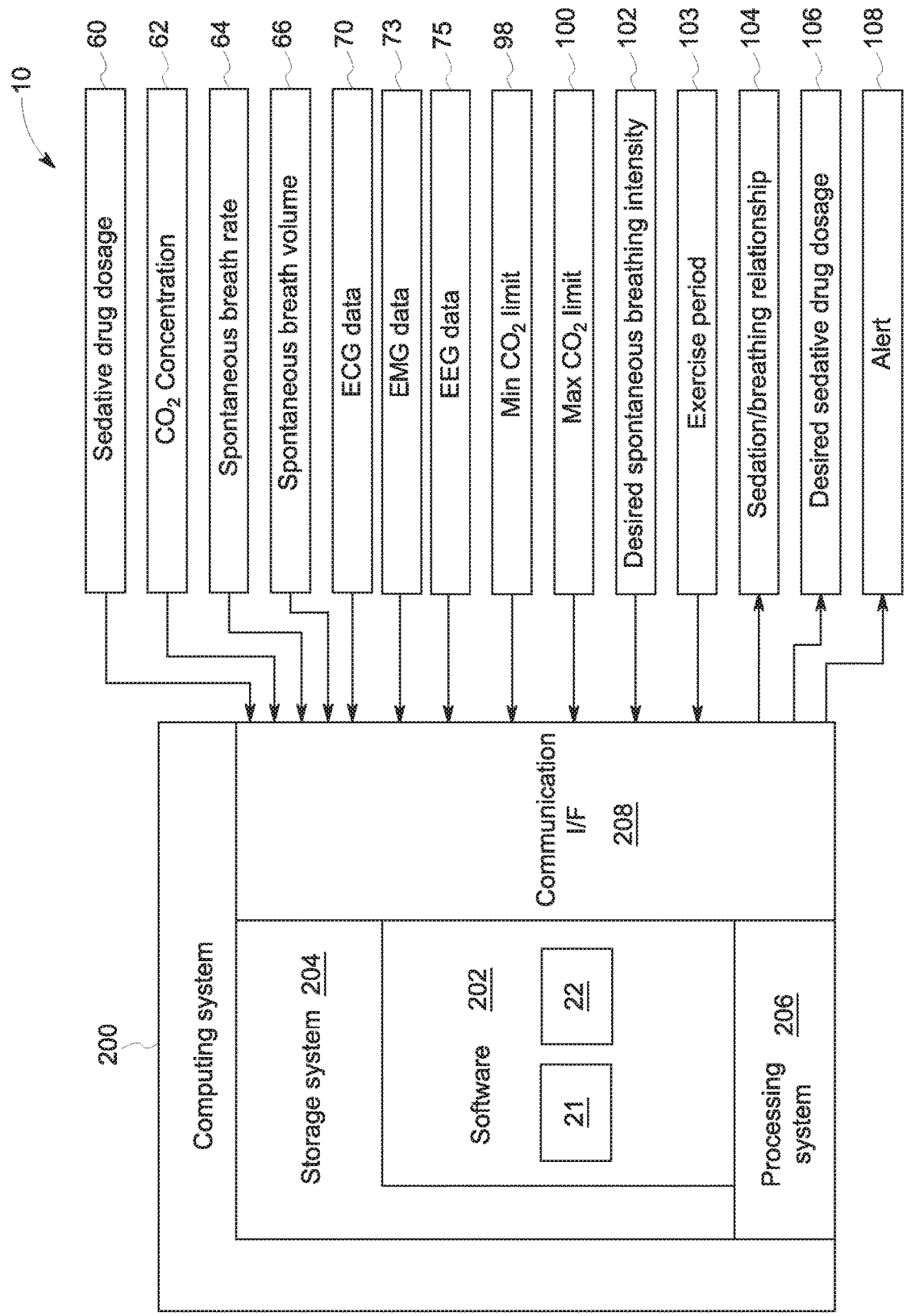
FIG. 2 is a schematic diagram of a computing system to be incorporated in a system for controlling patient sedation and spontaneous breathing intensity.

To maintain the optimal patient $CO_2$ level, the amount of ventilation must be adjusted to meet a $CO_2$ clearance demand. Furthermore, during mechanical ventilation increases in the amount of ventilation must be divided between the breath rate and volume, finding the optimal balance between minimal lung pressure and total amount of ventilation. Likewise, patient spontaneous inspiration activity depends on the level of patient sedation and patient respiratory center $CO_2$ stimulus. In the respiratory center, the balance of sedative status and $CO_2$ level determines respiratory drive, which is reflected as the spontaneous inspiration efforts of patients. The sedative status is measured as any value that indicates the sedative drug effect on the patient's physiology, including the patient's respiratory drive. This drug effect, or level of sedation, may be indicated by, for example, by the sedative drug dosage 60 delivered to the patient (FIG. 2). In other examples, it is determined by the measured or the modelled sedative drug concentration of the patient, or by the sedative drug effect estimated by the EEG/fEMG signal indicator, or by any combination of the above-mentioned measures.

The sedative drugs dampen the spontaneous activity, whereas the $CO_2$ concentration stimulates the spontaneous activity. Sensitivity to these contributors varies among patients, and is an individual characteristic. Adjusting the sedative status by changing administered sedative drug dosage and the respective patient drug concentration, modifies the patient-specific $CO_2$ level required for triggering spontaneous ventilation. Reduction in the drug delivery and the respective patient sedative drug concentration decreases patient respiratory center trigger $CO_2$ concentration (e.g., 326 in FIG. 3). When patient $CO_2$ concentration rises above the patient's respiratory trigger $CO_2$ concentration, spontaneous inspiration action begins. Inspiration efforts will continue as long as the patient $CO_2$ concentration remains above the respiratory trigger $CO_2$ concentration.

Respiratory center regulates spontaneous breathing intensity, including breath tidal volume and respiration rate, to maintain the patient's $CO_2$ at a level characteristic for that patient. This process typically maintains a blood pH value close to the neutral level of 7.4. Strengthening the stimulus by increasing a patient's $CO_2$ concentration increases patient breathing activity, which can be observed by increased breath rate and/or increased breath volume. The increased spontaneous breathing intensity reduces the patient $CO_2$ level until the $CO_2$ stimulus reaches a steady state determined by the current sedative drug concentration of the patient.

Patient treatment may require various levels of ventilation. In deep sedation, mechanical ventilation is adjusted to keep the patient $CO_2$ level below the respiratory center trigger $CO_2$ concentration. Typically, the targeted patient $CO_2$ level is 5-6 kPa, but with patients having lung-related problems this may be kept up to 10 kPa or higher by drug administration. The higher the patient $CO_2$ concentration, the larger the sedative drug concentration needed to dampen the respiratory stimulus. In deep sedation, patient EEG and/or facial EMG activity can be used for estimating the sedation level, or effect, on the patient's central nervous system.

As described in more detail below, the disclosed method and system assists in weaning the patient from mechanical ventilation by promoting patient spontaneous breathing activity. The disclosed solution records the sedative status of the patient with respectively measured patient $CO_2$ level and intensity of spontaneous breathing. Once recorded, this relationship can be utilized to control the patient's sedative status in order to optimize transitions between different ventilation phases. For example, the sedative drug dosage may be decreased and the ventilation therapy adjusted, such as to allow pressure support of spontaneously-triggered patient inspiration. When spontaneous inspirations are identified, the respective sedative drug dosage, and/or patient sedative drug concentration, and/or sedation level based on EEG and/or fEMG data is recorded along with the patient's $CO_2$ concentration. All such values are recorded for each sedative drug dosage administered to the patient during the recording period. Any change in sedative drug dosage will result in a new sedation status, or sedation level, and a new respiratory trigger $CO_2$ concentration at that sedative status. Likewise, the spontaneous intensity of any respiratory action that is present will also change as a result of the change in drug dosage.

As the sedative drug information and the patient's corresponding $CO_2$ concentration and/or sedation level (e.g. based on EEG and/or facial EMG data) are recorded over time and at various sedative statuses of the patient, the data values are merged together to define a sedation/breathing relationship for the patient. The sedation/breathing relationship is the relationship between the patient's spontaneous breathing intensity and the sedative status for the patient. For example, the sedation/breathing relationship may be extrapolated from the available measured data during patient treatment, including the correlated sedative status (e.g., the sedative drug dosage 60 or sedation level values) and spontaneous breathing intensity values. The sedation/breathing relationship information can then be used to accurately and appropriately control patient sedation in order to achieve a desired spontaneous breathing intensity.

The desired spontaneous breathing intensity may be controlled as part of a weaning process, to remove a patient from a ventilator, or as part of an exercise process to prevent respiratory muscle atrophy for a mechanically ventilated patient. For example, pressure supported spontaneous breathing may include phases of various patient breathing intensities. The sedation/breathing relationship defined for the patient can be utilized to maintain the patient sedation at a level that allows repetitive transitions between ventilation phases, such as to provide periodic exercise and/or to test the patient's readiness for weaning from mechanical ventilation. Likewise, the sedation/breathing relationship defined for the patient can be used to determine an appropriate minimum sedative status that sufficiently suppresses the patient's respiratory drive in order to provide a relaxation period in order to avoid patient fatigue.

Specifically, a desired sedative status can be calculated based on the sedation/breathing relationship in order to achieve the desired spontaneous breathing intensity. The disclosed control methods are especially valuable in connection with sedative drugs that have a fast response time and a slow concentration decay. With such drugs, off-target in delivery change may result in excessive breathing load (dosage is too low) or suppress the spontaneous action (dosage is too high).

The intensity of the patient's spontaneous inspiration is measured, such as based on spontaneous breath rate and/or spontaneous breath volume. The intensity of the spontaneous action can also be measured, for example, as occlusion pressure 100 ms after the breath initiation (i.e., P0.1), or a change in measured patient compliance value or change in inspiration tidal volume if support pressure remains constant. To the extent that ventilation support is present, the intensity of patient spontaneous action to maintain the $CO_2$ concentration depends on the ventilator-applied pressure support. The larger the pressure support, the smaller the amount of work required by the patient (i.e., the smaller the patient's spontaneous breathing intensity). Thus, any provided ventilation support should be accounted for as part of the spontaneous breathing intensity value.

Figure 1:
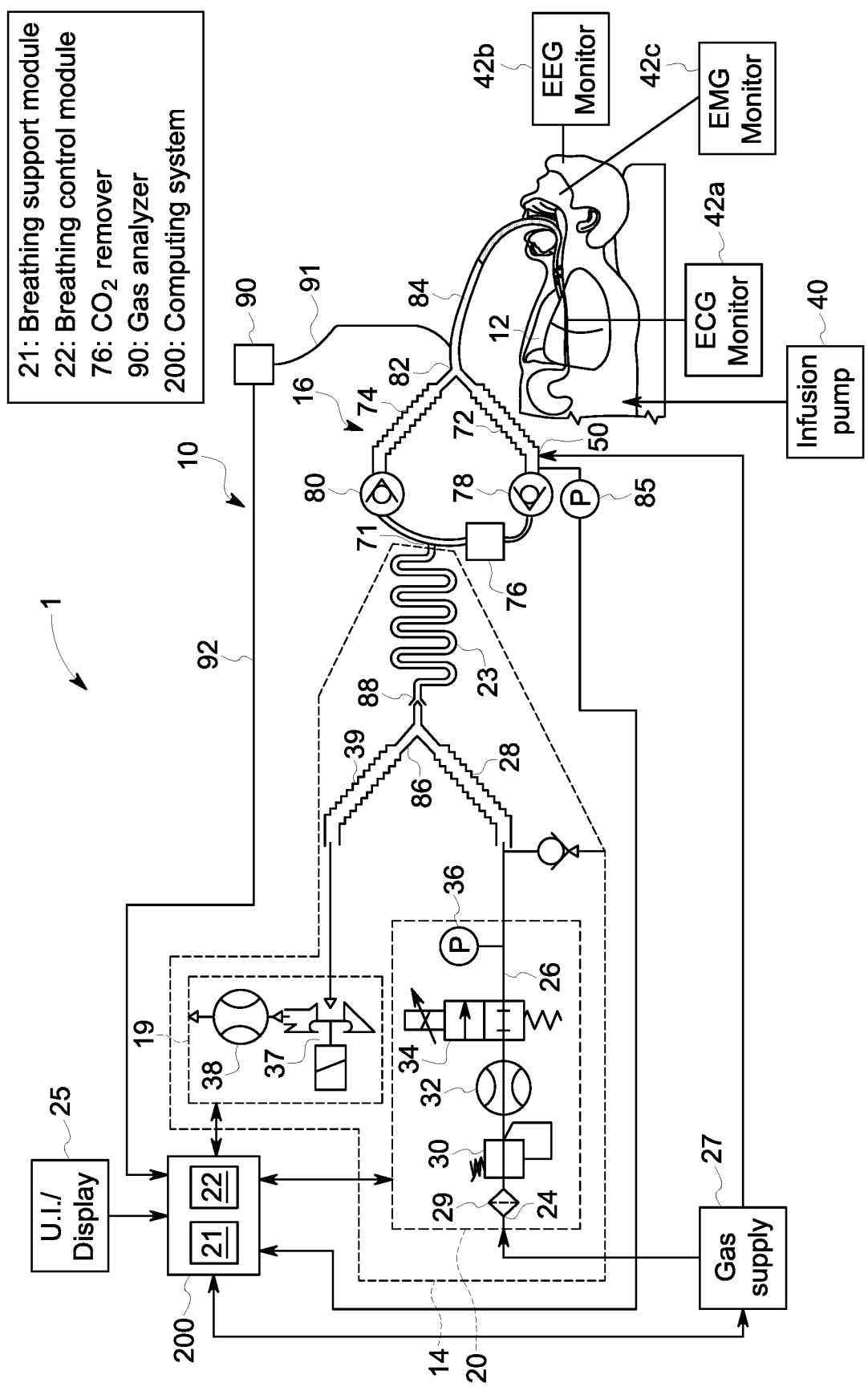
FIG. 1 is a schematic diagram depicting one embodiment of a system for controlling patient sedation and spontaneous breathing intensity.

FIG. 1 provides one embodiment of a system 1 for controlling patient sedation and spontaneous breathing intensity. The system 1 includes a ventilator system 10 that provides an inspiration gas to the patient 12 utilizing a re-breathing system. The ventilator system 10 comprises a machine ventilator circuit 14 for assisting breathing functions of the patient, a breathing circuit 16 for connecting lungs of the patient and the machine ventilator circuit 14 to exchange the gas in the lungs, and spontaneous breathing modules 21 and 22 for controlling operation of the ventilator system 10 according to the patient's ventilation needs. The ventilator system 10 shown in FIG. 1 includes a gas supply 27 for supplying breathing gases to the patient, which include a fresh gas, oxygen ($O_2$), and/or inhalational anesthetic agents, such as Desflurane, Isoflurane, nitrous oxide, Sevoflurane, Xenon, etc. The system 1 may further include a user interface 25 for entering any information needed while ventilating the patient, as well as for displaying patient information, including the current sedative status (e.g., sedative drug dosage, sedative drug concentration, or sedation level), spontaneous breathing intensity, $CO_2$ concentration, and a desired sedative status calculated by the system 1 based on a desired respiratory intensity for the patient.

The machine ventilator circuit 14 generally comprises an inspiration delivery unit 20 for delivering the pressure support gas needed to enable an inspiration of the patient, an expiration circuit 19 for controlling a discharge of the expiration gas and a reciprocating unit 23 (e.g., a bellows and bottle combination where the bellows are arranged within the bottle, or a long gas flow channel as shown in FIG. 1 for compressing the gas under a control of the drive gas pressure towards lungs of the patient to facilitate the inspiration). In certain embodiments, both the inspiration delivery unit 20 and the expiration circuit 19 may be controlled by one or both of the spontaneous breathing software modules 21, 22.

As illustrated in FIG. 1, the inspiration delivery unit 20 comprises a compressed gas interface 24 connected to a compressed gas supply 27. The compressed gas can be either oxygen or air. The inspiration delivery unit 20 also comprises a filter 29 for filtering impurities, a pressure regulator 30 for regulating a pressure of gases flowing from the gas interface, a flow sensor 32 for measuring an inspiration delivery flow from the gas interface and a flow control valve 34 for opening or closing the inspiration delivery flow. The flow sensor 32 and flow control valve 34 are each coupled to the computing system 200, to be received by the spontaneous breathing modules 21 and 22. Further, the inspiration delivery unit 20 may comprise a pressure sensor 36 for measuring the gas pressure flowing along the conduit 26 and an inspiration branch 28 towards the reciprocating unit 23. Thereby, the breath volume can be determined based on the gas flow and pressure. In other embodiments, the spontaneous breathing support module 21 and control module 22 may be configured and utilized in connection with an intensive care unit (ICU) ventilator, where the breathing circuit 16 is eliminated and the gas is delivered directly to the patient from connection point 88. In such an embodiment, two distinct inspiration control modules may be provided, one for controlling air delivery and the other for controlling $O_2$ delivery to the patient.

The gas supply 27 may supply fresh breathing gas to the gas outlet 50 in the breathing circuit. The gas supply 27 may include any number of one or more tanks or vessels containing gasses, which may be compressed gasses, to be delivered to the patient, such as oxygen, air, nitrous oxide, and/or volatile anesthesia agents. The gas supply 27 may further include a gas mixer to mix some or all of the various gasses being supplied to the patient, such as via the ventilator circuit 14 or before delivery to the gas outlet 50, and may comprise any number of filters, pressure regulators, air flow sensors, and air flow control valves, etc. as is well known in the relevant art.

The breathing circuit 16, which is operably connected to the machine ventilator circuit 14 at a breathing circuit connection 71 and to the fresh gas outlet 50, comprises an inspiration limb 72 for an inspired gas, an expiration limb 74 for an exhaled gas, a carbon dioxide ($CO_2$) remover 76 such as $CO_2$ absorber to remove or absorb carbon dioxide from the exhaled gas coming from the patient 12, a first one-way valve 78 for an inspired gas to allow an inspiration through the inspiration limb 72, a second one-way valve 80 for an expired gas to allow an expiration through the expiration limb 74, a branching unit 82 (such as a Y-piece) having at least three limbs, one of them being for the inspired gas, a second one being for the expired gas and a third one being for both the inspired and expired gases and being connectable to by means of the patient limb 84 to the lungs of the patient 12. Also the breathing circuit may comprise a pressure sensor 85 for measuring a pressure of the breathing circuit 16.

During the inspiration phase of the machine ventilation the expiration circuit 19 of the machine ventilator circuit 14 closes the expiration valve 37, such as under the control of the spontaneous breathing support module 21. This guides the inspiration gas flow from the inspiration delivery unit 20 through the inspiration branch 28 of a gas branching connector 86 and through the connection 88 of the reciprocating unit 23 pushing the breathing gas out from the breathing circuit connection 71 to the breathing circuit 16. The inspiration gas delivery unit 20 controlled by the spontaneous breathing support module 21 delivers the gas flow either to reach the given gas volume or a pressure at breathing circuit measured. For this control, the flow sensor 32 for measuring the inspiration flow and the pressure sensor 85 of the breathing circuit 16 are used.

The ventilator system 10 also includes a gas analyzer 90 to measure the concentrations of various gasses in the expiration gas from the patient, including the $CO_2$ concentration. Such analyzer can be either a side-stream type that suctions a sample gas stream through sampling line 91 for analysis, or a mainstream type where the analysis occurs in the gas stream in the patient limb 84. The analyzer communicates gas concentrations to the computing system 200 through communication line 92. Gas analyzer 90 can be of any known type able to measure particular gas concentrations. For example, the gas analyzer 90 may be an infrared absorption analyzer configured to measure $CO_2$ concentration in the gases exhaled by the patient 12.

In embodiments where respiration support is provided, the breathing circuit 16 and the patient lungs are pressurized. For the expiration under the control of the spontaneous breathing support module 21, the inspiration delivery flow control valve 34 is closed stopping the inspiration delivery and the expiration valve 37 is opened to allow the gas release from the expiration branch 39 of the drive gas branching connector 86 and further through the connection 88 from the reciprocating unit 23. This allows the pressure release and breathing gas flow from breathing circuit 16 and the lungs of the patient 12 to the reciprocating unit 23. The breathing gas flows from the patient 12 through the patient limb 84, the branching unit 82, the expiration limb 74, the second one-way valve 80 for the expired gas and the breathing circuit connection 71 to the reciprocating unit 23. The pressure release is controlled for a desired expiration pressure, such as a positive end expiration pressure (PEEP) target. For this control, the spontaneous breathing support module 21 uses the breathing circuit pressure measured by the pressure sensor 85 and the expiration valve 37. The expiration gas flow may be measured using the flow sensor 38 located at the outlet the expiration valve 37 as shown in FIG. 1 or at any location on the expiration pathway from patient limb 84 to the expiration valve 37. In other embodiments, the ventilation support delivered to the patient to assist spontaneous breathing may be controlled by other means, such as by clinician control of a PEEP value. In any event, the ventilation support, or support pressure, supplied to the patient is preferably be accounted for in the spontaneous breathing intensity value calculated for the patient.

The expiration circuit 19 comprises an expiration valve 37 for discharging the expiration gas and a flow sensor 38, which is optional, for measuring the flow discharged through the expiration valve 37. The expiration circuit is in flow connection along an expiration branch 39 with the reciprocating unit 23.

The system 1 further includes an infusion pump 40 configured to administer sedative drugs intravenously to the patient 12. To provide just on example, the infusion pump 40 may be configured to deliver Propofol to the patient 12. The infusion pump may be, for example, a target controlled infusion (TCI) system. The system 1 further includes patient monitors for measuring physiological parameters from the patient during sedation. In the depicted embodiment, the system 1 includes an electrocardiograph (ECG) monitor 42$a$ and an electroencephalograph (EEG) monitor 42$b$ and an electromyograph (EMG) monitor 42$c$ (such as a facial EMG monitor). For example, the ECG monitor 42 measures cardiac potentials, heart rate and/or heart rate variability of the patient 12. The EEG monitor 42$b$ may be configured to measure neural potentials and to determine patient parameters based thereon, such as Entropy or other depth-of-anesthesia indicator values. The EMG monitor 42$c$ may be configured to measure muscle activity of the patient, such as facial muscle activity. The fEMG activity can be used as an indicator of, for example, the patient's response to stimuli.

The infusion pump 40 and patient monitors 42$a$, 42$b$, 42$c$ may be configured to communicate with the computing system 200. In certain embodiments, such as in a TCI system, the computing system 200 and infusion pump 40 are communicatively connected, such the infusion pump 40 communicates with the computing system 200 to transmit and/or receive a current and/or desired sedative status for the patient 12. Such control operations between the computing system 200 and the infusion pump 40 may be automatic, or the system 1 may be configured such that a clinician sets the sedative status (e.g., sets a sedative drug dosage, sedative drug concentration, or a sedation level based on physiologic information measured from the patient at the user interface display 25) which is then communicated to the infusion pump 40 via the computing system 200. In still other embodiments, the clinician may set the sedative drug dosage directly at the infusion pump 40. In such embodiments, the infusion pump may communicate that sedative drug dosage value to the computing system 200 for use by the various software modules 21, 22. Alternatively, the infusion pump 40 may not be communicatively connected to the computing system 200, and thus a clinician may be required to input the sedative drug dosage setting to the computing system 200, such as via the user interface 25, and the infusion pump 40 may be separately set and controlled by the clinician. The patient monitor (42a, 42b) may also be communicatively connected to the computing system 200 such that the spontaneous breathing control module 22 receives the appropriate physiological parameters based on the physiological measurement data obtained by the patient monitors 42a, 42b, 42c.

FIG. 2 provides a system diagram of an exemplary computing system 200 incorporated in a system 1 or controlling patient sedation and spontaneous breathing intensity. The exemplary computing system 200 includes two software modules, a spontaneous breathing support module 21 and a spontaneous breathing control module 22, which are executable as described herein. The spontaneous breathing control module 22 is configured to determine a sedation/breathing relationship 104 between the patient's spontaneous breathing intensity and the sedative drug dosage 60 based on the patient's $CO_2$ concentration 62, the patient's spontaneous breath rate 64, spontaneous breath volume 66, and a sedation level based on ECG data 70, fEMG data 73, and/or EEG data 75 measured from the patient at the current drug dosage. The spontaneous breathing control module 22 may determine a preferred $CO_2$ level for the patient based on the patient's $CO_2$ concentration at each respective sedative drug dosage 60. For example, a first preferred $CO_2$ level may be based on $CO_2$ concentration measurements recorded over a period of time when the patient is receiving the first sedative drug dosage. To provide one specific example, the preferred $CO_2$ level may be determined based on an average end-tidal $CO_2$ ($EtCO_2$) concentration measured for the patient during the period of time while the patient remained at the respective sedative status.

The spontaneous breathing control module 22 may then determine a spontaneous breathing intensity at the respective preferred $CO_2$ level and sedative status. For example, the first spontaneous breathing intensity may be based on a spontaneous breath rate 64 and/or a spontaneous breath volume 66. If breathing support is being supplied to the patient, the spontaneous breath intensity may further be determined based on the amount of breathing assistance, e.g., the support pressure being supplied to the patient.

Likewise, the same thing may be performed when the patient is at a second sedative status, thereby to determine a second preferred $CO_2$ level and a second spontaneous breathing intensity. The spontaneous breathing control module 22 then defines a sedation/breathing relationship 104 between spontaneous breathing intensity and sedative status for the patient. As exemplified in the graphs 301, 305, 314 at FIG. 3, the sedation breathing relationship 322 may be determined by interpolating at least a first point 313 representing the first sedative drug dosage 311 and the first spontaneous breathing intensity 312 and a second point 320 representing the second sedative drug dosage 318 and the second spontaneous breathing intensity 319.

When a clinician decides that a weaning trial or a respiratory exercise session is appropriate, the clinician may instruct a desired spontaneous breathing intensity 102, such as by providing appropriate input via the user interface 25. The desired sedative status is then determined by utilizing the fitting 322, i.e., in this example, the desired sedative status is the sedative drug dosage 106 value corresponding to the desired spontaneous breathing intensity 102 on the fitting line 322. In certain embodiments, the spontaneous breathing control module 22 may be configured to automatically control the drug delivery devices in the system, including the infusion pump 40 and/or the delivery of anesthesia gas from the gas supply 27, to automatically deliver the desired sedative drug dosage 106 to the patient 12 so as to achieve the desired spontaneous breathing intensity 102.

In certain embodiments, the system 1 may be capable of providing automated spontaneous breathing support for assistance in weaning a patient off of a ventilator and/or providing respiratory exercise for the patient 12. In such an embodiment, the computing system 200 may include a spontaneous breathing support module 21 that determines and maintains an appropriate breathing support pressure for the patient based on the patient's needs, such as to allow the patient to maintain their preferred $CO_2$ level at the respective sedative status. Namely, the spontaneous breathing support module 21 adapts to the patient respiratory center response to provide an appropriate support pressure to sustain the desired $CO_2$ level for the patient. Information regarding the patient's respiratory stimulus, or spontaneous intensity, is provided by the patient's $CO_2$ level, such as by the measured $EtCO_2$ and/or based on measurements or estimations of the patient's arterial blood $CO_2$ level (e.g., $PaCO_2$). Examples of such control methods that may be executed by the spontaneous breathing support module 21 are provide at U.S. patent application Ser. No. 15/423,340, which is hereby incorporated by reference in its entirety. Such breathing support control algorithms can be further utilized and adapted to provide a desired spontaneous breathing intensity for the patient and avoid patient fatigue.

The computing system 200 includes a processing system 206, storage system 204, software 202, and a communication interface 208. The processing system 206 loads and executes software 202 from the storage system 204, including the spontaneous breathing support module 21 and the spontaneous breathing control module 22 which are applications within the software 202. The modules 21 and 22 include computer-readable instructions that, when executed by the computing system 200 (including the processing system 206), direct the processing system 206 to operate as described in herein in further detail, including to execute the steps to determine a desired drug dosage in order to achieve a desired spontaneous breathing intensity, and to determine and provide an appropriate support pressure to assist the patient's respiration.

Although the computing system 200 as depicted in FIG. 2 includes one software 202 encapsulating one spontaneous breathing support module 21 and one spontaneous breathing control module 22, it should be understood that one or more software elements having a single software module or more than two modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor, which may be a microprocessor, a general purpose central processing unit, and application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and other elements within the system 1, such as elements of the ventilator circuit 14, the gas supply 27, the breathing circuit 16, the gas analyzer 90, the infusion pump 40, the patient monitor(s) 42a, 42b, 42c and/or the user interface 25. For example, the communication interface 208 receives the patient's $CO_2$ concentration, spontaneous breath rate 64, spontaneous breath volume 66, and physiological data measured from the patient via respective devices. The communication interface 208 may also communicate the desired sedative drug dosage 106 to the drug delivery device(s) 10, 40 based on the desired sedative status. In embodiments where pressure support is controlled and determined at the computing system 200, such as by the spontaneous breathing support module 21, the communication interface may also communicate a support pressure command to the ventilator circuit 14 so that the appropriate ventilation support is provided to the patient. In certain embodiments, the communication interface may also communicate a control signal to the user interface 25 instructing display of the desired sedative drug dosage 106 and other values determined by the modules 21, 22, and/or instructing generation of an alert 108, such as when the spontaneous breathing control module 22 determines that the patient's respiratory stimulus is too high or too low.

Additionally, the communication interface 208 may output the sedation/breathing relationship 104 and/or the preferred $CO_2$ levels determined by the spontaneous breathing control module 22 at the various sedative drug dosages 60, for example to display one or more of the values on the display of the user interface 25 and/or so that the values can be stored in the patient's medical record. In certain embodiments, the communication interface 208 may also receive a minimum $CO_2$ limit 98 and maximum $CO_2$ limit 100 for the patient for setting upper and lower bounds for the $CO_2$ concentrations that will be tolerated. For example, the minimum $CO_2$ limit 98 and maximum $CO_2$ limit 100 may be inputted by a clinician via the user interface 25, or by some other means, which will set the bounds within which the patient's $CO_2$ will be allowed to vary, such as during the mechanical ventilation weaning process or during respiratory exercises.

The user interface 25, which includes a display device, is configured to receive input from a clinician, such as regarding the timing and desired intensity of weaning trials and/or respiratory exercise sessions, and to set the maximum $CO_2$ limit 100 and minimum $CO_2$ limit 98. The user interface may also be configured to produce one or more alerts to the clinician, such as an alert 108 the respiratory drive is outside of the predetermined acceptable range. The alert 108 may include a visual alert on a digital display and/or an audio alert through speakers. The user interface 25 may include, in addition to the display device, a mouse, a keyboard, a voice input device, a touch input device (such as a touch pad or touch screen) for receiving a gesture from a user, a motion input device for detecting non-touch gestures and other motions by a user, and other comparable input devices and associated processing elements capable of receiving input from a user, such as a clinician. Speakers, printers, haptic devices and other types of output devices may also be included in the user interface 25.

Both patient spontaneous action and ventilator pressure support contribute to the breath volume, e.g., tidal volume, but only the patient's contribution to the breath volume indicates the strength of the patient's spontaneous breathing intensity. The portion of the breath volume attributable to the patient can be isolated from the ventilator contribution by using patient compliance, a relationship of changes in lung volume to lung pressure, instead of breath volume, as indicator for the spontaneous breathing intensity, or respiratory drive. The ventilation system 10 measures the breath volume, which includes both the patient's respiratory drive and the ventilator pressure support contribution. Spontaneous action causes negative pressure in the lungs and influx of breathing gas, but the ventilation pressure measurement can identify only the positive support pressure and the total amount of gas breathed in by the patient. Patient compliance can be used as the spontaneous breathing intensity value, which accounts for both the pressure support contribution and the support volume and is determined by the following equation:

$$C = \frac{TV}{dP} = \frac{TV_{spont} + TV_{supp}}{P_{supp}}$$

The numerator in the patient compliance calculation is the sum of spontaneous tidal volume and ventilator-driven volume, whereas the denominator corresponds to the ventilator pressure support only. $TV_{spont}$ is the breath volume contributing to patient spontaneous breath, $TV_{supp}$ is the ventilator pressure support contribution, and $P_{supp}$ is the ventilator support pressure. Accordingly, the patient compliance increases as the un-measurable negative pressure in the lungs increases the $TV_{spont}$ i.e., the larger the patient's respiratory drive is the larger the patient compliance will be.

Ventilation during weaning and/or respiratory exercise may vary between full mechanical ventilation and supported or unsupported spontaneous breathing, such as by utilizing supported spontaneous breathing as a variable transition mechanism between fully supported and unsupported spontaneous breathing. The spontaneous support may further include phases of various spontaneous breathing intensities, where the support pressure is decreased in order to increase the patient's contribution to the breathing and the support pressure is increased to decrease the patient's contribution to the breathing, such as to avoid fatiguing the patient. Since the patient's response to the various sedative statuses are known, i.e., the sedation/breathing relationship 104 is known, the desired sedative status, including a desired sedative drug dosage 106, can be determined for the desired spontaneous breathing intensity 102 during reduction or removal of support volume. The delivery of support volume can then be controlled to control the spontaneous breathing intensity as desired by decreasing the ventilation support pressure to increase the spontaneous activity and then increasing the ventilation support pressure to keep the patient $CO_2$ concentration below the trigger $CO_2$ concentration at the respective drug dosage and thus induce a relaxation phase that limits the patient's spontaneous breathing activity.

Figure 3:
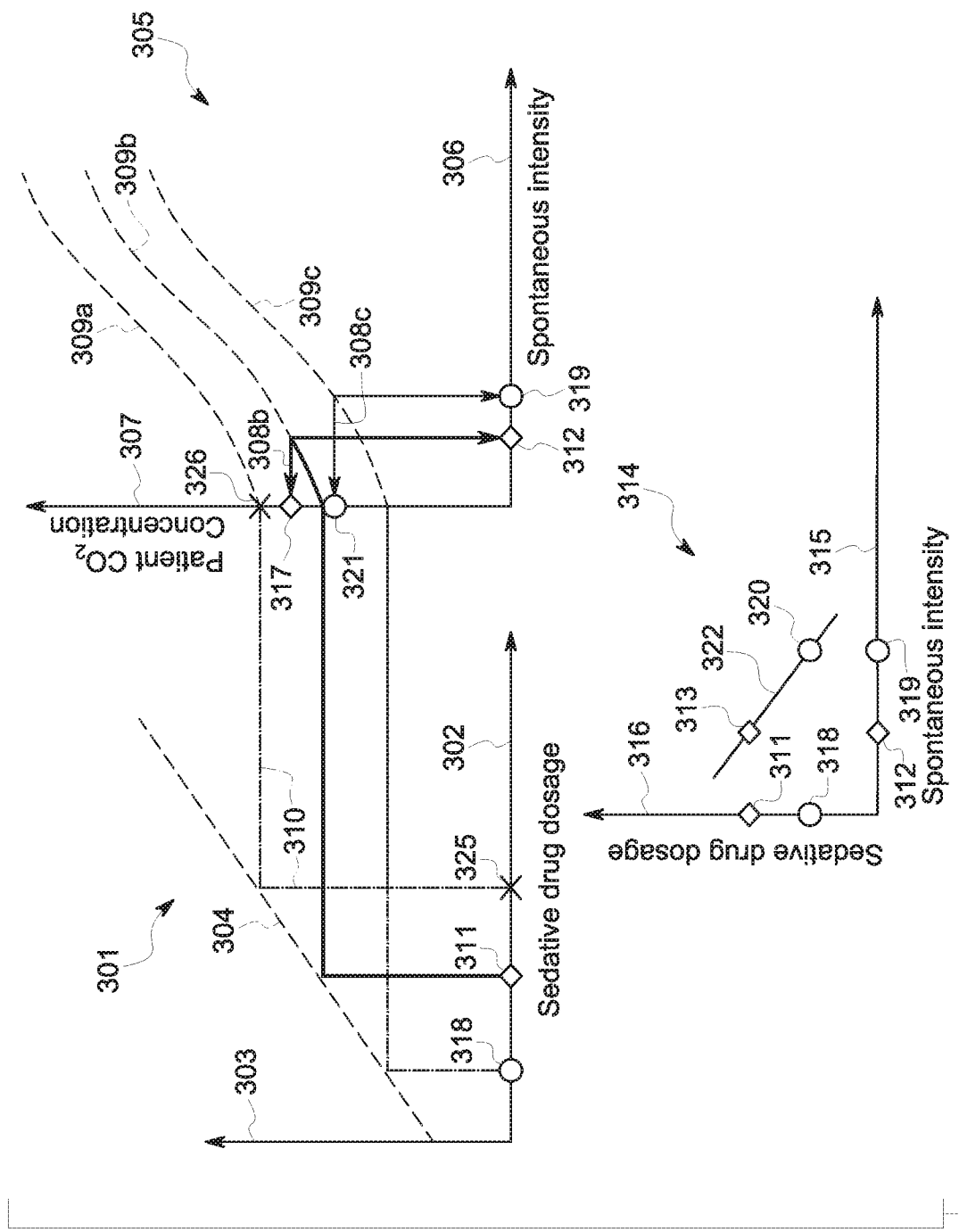
FIG. 3 is a set of graphs depicting exemplary control operation of a spontaneous breathing control module.

FIG. 3 graphically represents methods and logic that may be executed by the spontaneous breathing control module 22. Graph 301 describes the relationship, line 304, between sedative status (exemplified as sedative drug dosage on abscissa 302) and respiratory center trigger $CO_2$ concentration (on ordinate 303). This line demonstrates the minimum $CO_2$ concentration at which the spontaneous inspiration trigger occurs, the respiratory trigger $CO_2$ concentration, at a range of sedative statuses resulting from the depicted range of sedative drug dosages.

Graph 305 presents relationships between patient spontaneous breathing intensity on abscissa 306 and patient $CO_2$ concentration on ordinate 307, which are drug-dosage dependant relationships. Curvatures 309a-c describe the characteristic behaviour of respiratory center stimulus levels (the $CO_2$ concentrations on ordinate 307), the spontaneous breathing intensity (abscissa 306), at different sedative statuses. The sedative status determines the vertical placing of this curvature. Every patient has a preferred $CO_2$ level 308b, 308c where patient $CO_2$ concentration and spontaneous breathing intensity are balanced. Curvatures 309b and 309c present balanced $CO_2$ spontaneous breathing intensity levels at drug doses 311 and 318, correspondingly.

To illustrate the drug-dosage dependency of the relationship between respiratory stimulus ($CO_2$ concentration) and spontaneous breathing intensity for the patient, line 310 extends from a drug dosage 325 on abscissa of graph 301 through line 304 determining the minimum patient $CO_2$ concentration 326 to trigger spontaneous breath at that drug dosage 325. Transferring that trigger $CO_2$ concentration 326 to graph 305 determines the position of the respiratory center curve 309a representing the characteristic behavior depicted in graph 305. When mechanical ventilation is adjusted such that patient $CO_2$ concentration is maintained below curve 309a, as long as the patient's sedative status is maintained at the respective sedative drug dosage 325, no spontaneous action appears.

Reducing sedative status to value 311 reduces the characteristic behavior from 309a to 309b. As expressed on graph 305, the line 309b is below patient $CO_2$ concentration 317. The patient's spontaneous breathing action is triggered resulting in spontaneous breathing intensity 312. The abscissa values at point 311 and point 312 yield a first relationship point 313 on graph 314, which presents relationship between spontaneous intensity (on abscissa 315) and sedative status (e.g., sedative drug dosage on ordinate 316). In certain embodiments, the respective patient $CO_2$ concentration 317 may be merged on this data point (such as represented by the $EtCO_2$ or $PaCO_2$ for the patient at the respective spontaneous intensity and sedative drug dosage).

Further reduction of sedative status to value 318 decreases the position of the respiratory center characteristic curve to 309c. This intensifies the spontaneous breathing needed to maintain the patient's preferred $CO_2$ level 308c, resulting in spontaneous breathing intensity 319. The points 318 and 319 yield a second data point 320 on the graph 314. As described above, this data point may also be merged with the respective $CO_2$ concentration 321.

The sedative status, including the sedative drug dosage and/or sedation level, accounts for all drugs affecting to respiratory system. Administration of respiratory depressant, e.g. Propofol, has positive impact to sedative drug dosage 302 and 316, whereas administration of respiratory stimulant, e.g. Doxapram, has negative impact. In many cases, two or more agents (which may be a mix of inhalation agents and/or infusion agents) are administered to the patient. Thus, the sedative drug dosage may include a dosage amount for each of the one or more drugs being delivered to the patient. Alternatively or additionally, where TCI control is implemented, the sedative drug dosage may include a target blood concentration for the one or more sedative drugs being delivered to the patient via TCI control. Where sedative status is indicated and controlled based on sedation level, calculations may be conducted to provide a corresponding desired sedative drug dosage 60 for each of the one or more drugs based on the desired sedation level.

Data points 313 and 320 can then be used to define a relationship 322 between spontaneous breathing intensity and sedative status, the sedation/breathing relationship 104. This relationship 104 can be used to adjust patient sedation level in different phases of patient ventilation therapy aiming for different goals, to intensify breathing for exercise and weaning trials and reduce the breathing intensity for relaxation after these stressful phases.

The data available to the spontaneous breathing control module 22 for determination of the sedation/breathing relationship are sedative drug dosage 60, sedation level according to an EEG and/or fEMG derived sedation index, patient $CO_2$ concentration 62 (e.g. end-tidal $CO_2$ concentration), spontaneously triggered breath rate 64 and spontaneous breath volume 66 (or its surrogate).

It should be noted that, when collecting the data points to determine line 322, reasonable time is required to achieve steady state before recording the various data values. This time delay depends on the drug used, whether concentration is increased or decreased, and the amount of the change. Especially long time, the lead time, will be required when decreasing Propofol dosing after patient tissues have been saturated with the drug during prolonged delivery. A much shorter time will be required when using modern inhalation anaesthetics having low solubility. It should be further noted that the graphs 301 and 305 are presented here for qualitative demonstration purposes only, and may not be the mechanism by which the spontaneous breathing control module 22 operates to determine the desired sedative status, (e.g., desired sedative drug dosage 106).

Figure 4:
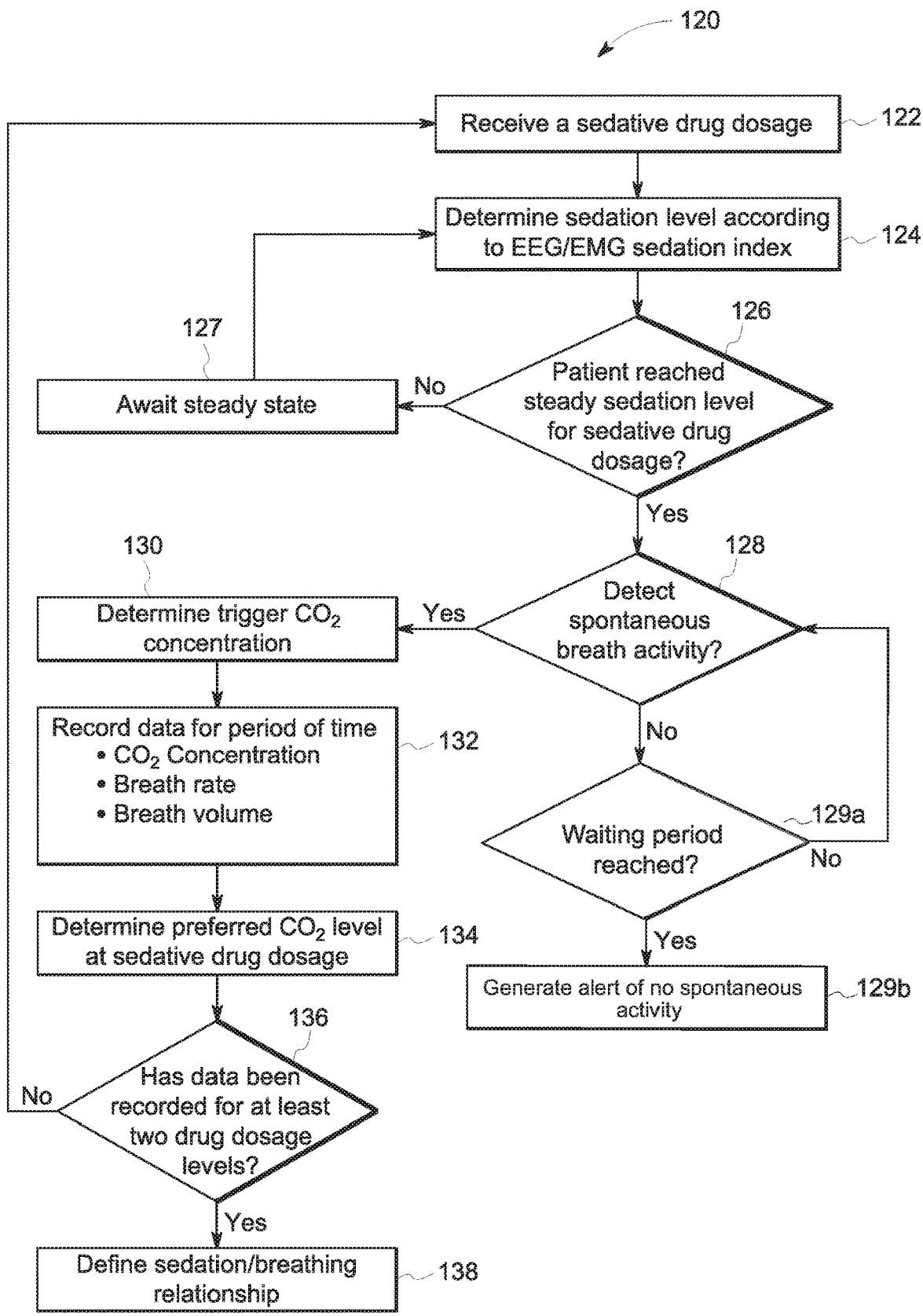
FIGS. 4-6 are flow charts depicting exemplary embodiments of methods, or portions thereof, of controlling sedation and spontaneous breathing intensity of a patient.
Figure 5:
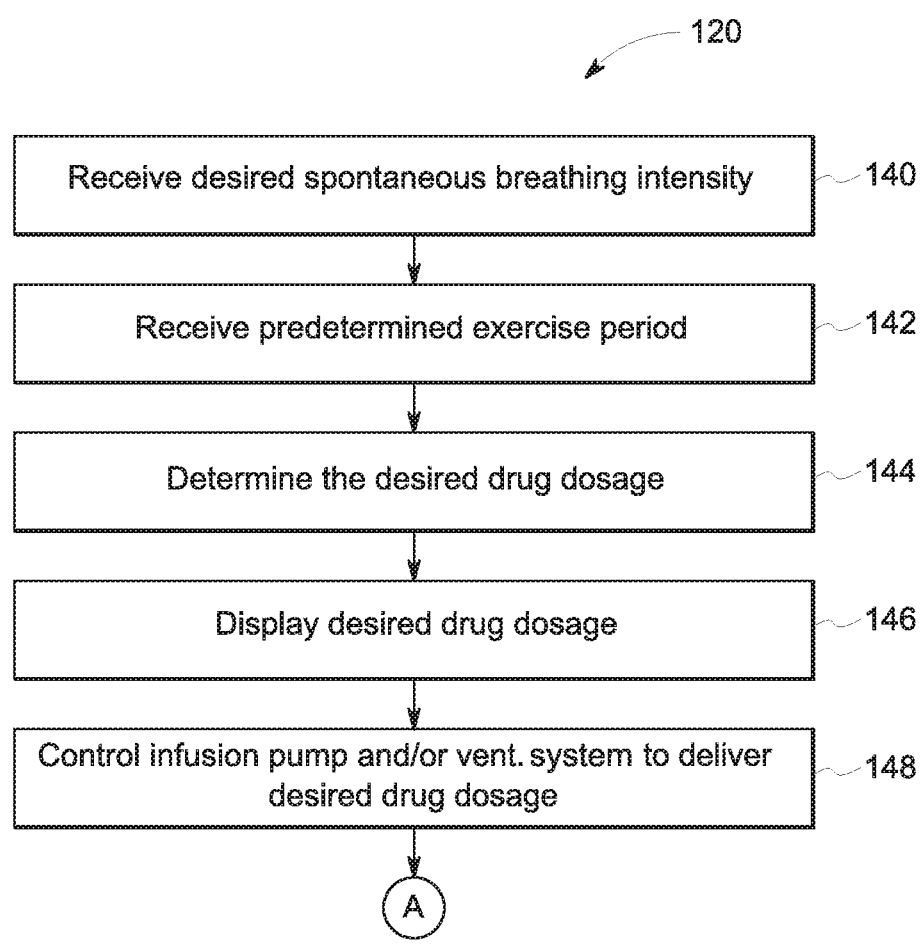
Figure 6:
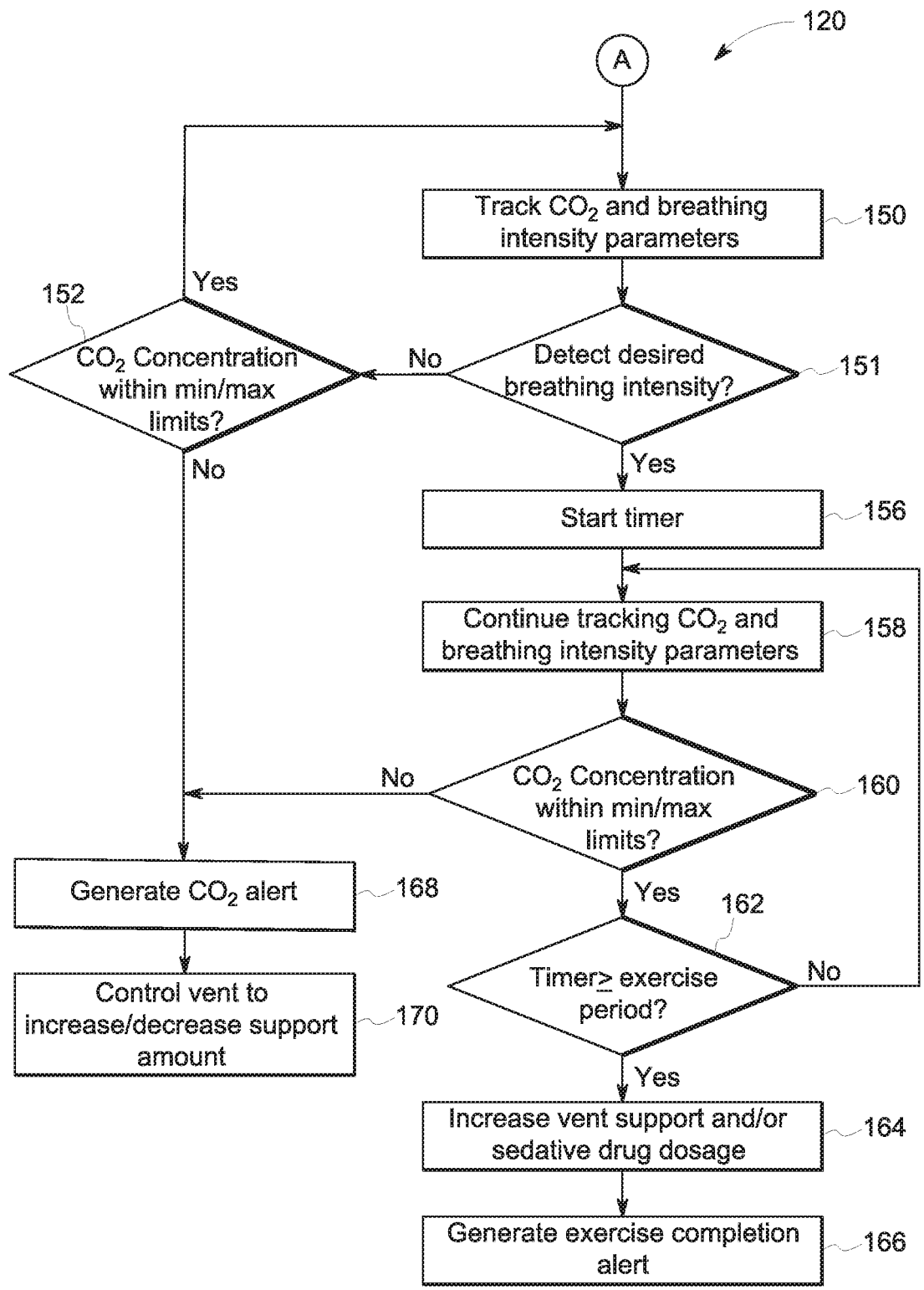

FIGS. 4-6 depict embodiments of methods 120, or portions thereof, for controlling sedation and spontaneous breathing intensity of a patient. The sedative status is received at step 122, such as a sedative drug dosage 60 set by a clinician or automatically controlled by an anesthesia control system. The sedation level is then determined at step 124 based on physiological signals, such as according to a sedation index utilizing EEG and/or fEMG data. The patient's $CO_2$ concentration, breath rate, and breath volume may also be monitored. Step 126 determines whether the patient has reached a steady sedation level for the sedative drug dosage. This step may be most necessary when one or more sedative drugs are being administered via infusion, such as Propofol. EEG and/or fEMG data determined at step 124 may be used to determine if the patient has reached steady state. If steady state has not been reached, the system may continue to monitor the patient at steps 124-127 until steady state is reached.

Once steady state is reached, spontaneous breathing activity should be detected. On automatic ventilation control support adjusts automatically to steady state between stimulus ($CO_2$) and spontaneous intensity. In manual ventilation control the support should remain unchanged. If spontaneous breathing activity is not detected from the patient within a waiting period at step 129a, then an alert may be generated at step 129b to notify a clinician that no spontaneous activity was produced and that the sedative status may need to be further reduced in order to generate spontaneous breath activity. Once spontaneous breathing activity is detected, then the current $CO_2$ concentration 62 is recorded at step 130, which is determined to be the stead state $CO_2$ concentration (e.g., 317 or 321 in FIG. 3). Physiological data is then recorded at step 132 for a period of time, including $CO_2$ concentration, spontaneous breath rate, spontaneous breath volume, EEG and/or fEMG data, and drug effect site concentration, if TCI pump is in use. A preferred $CO_2$ level is then determined at step 134 for the respective sedative drug dosage. For example, the preferred $CO_2$ level may be determined based on the $CO_2$ concentration data recorded over the period of time, such as an average or median level, a filtered average, or some other value calculated based on the $CO_2$ concentration for the patient over the period of time at the respective sedative drug dosage. The system checks at step 136 whether sufficient data has been recorded in order to define the sedation/breathing relationship. For example, the sedation/breathing relationship may be defined based on two or more sedative drug dosage and spontaneous breathing intensity points measured at different drug dosage levels. Once sufficient data has been recorded, then the sedation/breathing relationship is defined at step 138. That definition may be refined as additional data is added.

Once the sedation/breathing relationship is defined, it can be utilized to control sedation to thereby control the patient's breathing intensity. A spontaneous breathing intensity is received at step 140, such as based on a clinician input to initiate a patient respiratory exercise session. A predetermined exercise period may also be received at step 142, such as a period of time at which the desired breathing intensity should be maintained and/or an interval at which the desired breathing intensity should be achieved. The desired drug dosage is then determined at step 144 based on the desired breathing intensity using the defined sedation/breathing relationship. The desired drug dosage is displayed at step 146, such as on the display of the user interface 25. In certain embodiments, the system may automatically control the infusion pump 40 and/or the ventilation system 10 in order to automatically deliver the desired the drug dosage.

Steps may then be executed to track the patient's $CO_2$ and breathing intensity parameters in order to provide a controlled respiratory exercise for the patient. FIG. 6 exemplifies such steps. The $CO_2$ and breathing intensity parameters are tracked at step 150, such as those inputs discussed at FIGS. 2 and 3. The spontaneous breathing control module 22 assesses the parameters at step 151 to determine whether and when the desired breathing intensity is reached. The module continually monitors the $CO_2$ concentration, step 152, to determine that it remains within the minimum and maximum $CO_2$ limits set for the patient. The spontaneous breathing control module 22 continues to track the $CO_2$ and breathing intensity parameters to ensure patient safety and assess whether the desired breathing intensity has been reached.

The $CO_2$ and breathing intensity parameters continue to be tracked at step 150 until the desired breathing intensity is reached at step 151. A timer is then started at step 156 to initiate tracking the timed exercise period. An exercise start time may also be identified and stored, such as for the patient's medical record. The spontaneous breathing control module 22 continues tracking the $CO_2$ and breathing intensity parameters at step 158 and insures at step 160 that the $CO_2$ concentration remains within the minimum and maximum $CO_2$ limits set for the patient. If at any point during the monitoring the $CO_2$ concentration falls below the minimum limit or exceeds the maximum limit, then a $CO_2$ alert may be generated at step 168 to alert a clinician of the problem. In certain embodiments, the ventilator may also be automatically controlled at step 170 to increase or decrease the support amount, depending on whether the $CO_2$ concentration is too low or too high.

Assuming that the $CO_2$ concentration remains within the limits, then the breathing intensity is maintained until the timer reaches the exercise period at step 162. At that point, patient relaxation may be induced at step 164 by increasing the ventilation support and/or increasing the sedative drug dosage provided to the patient. An exercise completion alert may be generated at step 166. Additionally, certain parameter and/or exercise tracking data may be saved to the patient's record and/or on the memory of the patient monitor in order to document the exercise session for review by a clinician. For example, the tracked $CO_2$ and breathing intensity parameters may be stored, along with the sedative drug dosage and sedation level in and around the relevant exercise period.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for controlling patient sedation and spontaneous breathing intensity, the system comprising:
   a ventilator system comprising:
      a ventilator circuit that outputs breathing gas from a gas supply to a patient and receives expiration gas from the patient;
   a spontaneous breathing control module executable on a processor and configured to:
      determine a first spontaneous breathing intensity at a first sedative status of the patient;
      determine a second spontaneous breathing intensity at a second sedative status of the patient;
      define a sedation/breathing relationship between spontaneous breathing intensity and sedative status for the patient based on the first sedative status and the first spontaneous breathing intensity, and the second sedative status and the second spontaneous breathing intensity;
      receive a desired spontaneous breathing intensity;
      determine a desired sedative status to achieve the desired spontaneous breathing intensity based on the sedation/breathing relationship; and generate an output related to the desired sedative status that achieves the desired spontaneous breathing intensity in the patient.

2. The system of claim 1, wherein generating the output related to the desired sedative status includes controlling a display device to display the desired sedative status that achieves the desired spontaneous breathing intensity in the patient, wherein the desired sedative status includes at least one of a desired sedative drug dosage or a desired sedation level.

3. The system of claim 1, wherein the spontaneous breathing control module is further configured to control at least one drug delivery device, wherein the output related to the desired sedative status includes a desired sedative drug dosage to the at least one drug delivery device so as to achieve the desired sedative status and the desired spontaneous breathing intensity in the patient.

4. The system of claim 1, wherein the sedation/breathing relationship is a fitting of at least a first point representing the first sedative status and the first spontaneous breathing intensity and a second point representing the second sedative status and the second spontaneous breathing intensity; and
wherein the desired sedative status is determined as a difference between a current sedative status and a sedative status corresponding to the desired spontaneous breathing intensity on the fitting.

5. The system of claim 1, further comprising:
a gas analyzer that measures a $CO_2$ content in the expiration gas and determines a $CO_2$ concentration;
wherein the spontaneous breathing control module is further configured to:
determine a first preferred $CO_2$ level for the patient based on the $CO_2$ concentration at the first sedative status;
wherein determining the first spontaneous breathing intensity includes determining a breathing intensity at the first preferred $CO_2$ level;
determine a second preferred $CO_2$ level for the patient based on the $CO_2$ concentration at the second sedative status; and
wherein determining the second spontaneous breathing intensity includes determining a breathing intensity at the second preferred $CO_2$ level.

6. The system of claim 5, wherein the first preferred $CO_2$ level is based on the $CO_2$ concentration measured over a first period of time at the first sedative status and the second preferred $CO_2$ level is determined based on the $CO_2$ concentration measured over a second period of time at the second sedative status.

7. The system of claim 6, wherein the first preferred $CO_2$ level is determined based on a first average end tidal $CO_2$ concentration for the patient during the first period of time and the second preferred $CO_2$ level is determined based on a second average end tidal $CO_2$ concentration for the patient during the second period of time.

8. The system of claim 1, wherein the spontaneous breathing control module is further configured to:
determine a respiratory trigger $CO_2$ concentration for the patient at the respective first or second sedative status; and
wherein the spontaneous breathing control module is further configured to determine a first preferred $CO_2$ level or a second preferred $CO_2$ level based on the respiratory trigger $CO_2$ concentration for the patient at the respective sedative status.

9. The system of claim 1, wherein the first sedative status, the second sedative status, and the desired sedative status include respective sedation levels determined for the patient;
wherein the spontaneous breathing control module is further configured to determine a first sedation level for the patient based on physiological data measured from the patient receiving a first sedative drug dosage, and a second sedation level for the patient based on physiological data measured from the patient receiving a second sedative drug dosage; and
wherein the physiological data includes at least one of EMG data or EEG data.

10. The system of claim 1, wherein spontaneous breathing intensity is determined based on at least one of a spontaneous breath rate and a spontaneous breath volume.

11. The system of claim 1, wherein the first sedative status, the second sedative status, and the desired sedative status include respective drug dosages delivered to the patient; and
wherein each of a first sedative drug dosage, a second sedative drug dosage, and a desired sedative drug dosage include a dosage amount for each of one or more sedative drugs being delivered to the patient.

12. The system of claim 1, wherein the first sedative status, the second sedative status, and the desired sedative status include respective drug dosages delivered to the patient; and
wherein each of a first sedative drug dosage, a second sedative drug dosage, and a desired sedative drug dosage include a target blood concentration value for each of one or more sedative drugs being delivered to the patient by target controlled infusion.

13. A method for controlling sedation and spontaneous breathing intensity of a patient, the method comprising:
receiving a first sedative status of the patient;
determining a first spontaneous breathing intensity at the first sedative status;
receiving a second sedative status of the patient;
determining a second spontaneous breathing intensity at the second sedative status;
defining a sedation/breathing relationship between spontaneous breathing intensity and sedative status for the patient based on the first sedative status and the first spontaneous breathing intensity and the second sedative status and the second spontaneous breathing intensity;
receiving a desired spontaneous breathing intensity;
determining a desired sedative status to achieve the desired spontaneous breathing intensity based on the sedation/breathing relationship; and
controlling one or more drug delivery devices based on the desired sedative status so as to achieve the desired spontaneous breathing intensity in the patient.

14. The method of claim 13, wherein the first, second, and desired sedative statuses each include at least one of a sedation level determined based on physiological data measured from the patient or a sedative drug dosage being delivered to the patient.

15. The method of claim 14, further comprising:
detecting a spontaneous inspiration of the patient; and
upon detecting the spontaneous inspiration, recording a current sedative drug dosage and/or a current sedation level and a current $CO_2$ concentration for the patient;
wherein the current sedation level is determined based on at least one of EMG data or EEG data measured from the patient.

16. The method of claim 15, further comprising determining a respiratory trigger $CO_2$ concentration for the patient at the current sedative drug dosage and/or the current sedation level based on the current $CO_2$ concentration for the patient.

17. The method of claim 16, further comprising:
controlling a ventilator system to decrease a ventilation support delivered to the patient to increase the patient's $CO_2$ concentration to at or above the respiratory trigger $CO_2$ concentration for the patient at a current sedative status to achieve the desired spontaneous intensity;
monitoring the patient's $CO_2$ concentration to determine whether is exceeds a maximum $CO_2$ limit; and
if the patient's $CO_2$ concentration exceeds the maximum $CO_2$ limit, controlling the ventilator system to increase the ventilation support delivered to the patient.

18. The method of claim 17, further comprising:
receiving a predetermined exercise period for which the desired spontaneous breathing intensity should be maintained; and
upon determining that the patient has maintained the desired spontaneous breathing intensity for the predetermined exercise period, controlling the ventilator system to increase the ventilation support delivered or controlling the one or more drug delivery devices to increase the sedative status.

19. The method of claim 16, further comprising:
determining a first preferred $CO_2$ level for the patient at a first sedative drug dosage;
determining a second preferred $CO_2$ level for the patient at a second sedative drug dosage; and
determining the preferred $CO_2$ level based further on the respiratory trigger $CO_2$ concentration for the patient at the respective sedative drug dosage.

20. The method of claim 13, wherein the sedation/breathing relationship is defined by interpolating between at least a first point representing the first sedative status and the first spontaneous breathing intensity and a second point representing the second sedative status and the second spontaneous breathing intensity; and
wherein the desired sedative status is a sedative status corresponding to the desired spontaneous breathing intensity on the interpolation representing the sedation/breathing relationship.

21. The method of claim 13, further comprising:
determining a first preferred $CO_2$ level for the patient at a first sedative drug dosage;
determining a second preferred $CO_2$ level for the patient at a second sedative drug dosage; and
wherein determining the first preferred $CO_2$ level includes determining a first average $CO_2$ concentration value over a first period of time at the first sedative status, and determining the second preferred $CO_2$ level includes determining a second average $CO_2$ concentration value over a second period of time at the second sedative status.

22. The method of claim 13, wherein spontaneous breathing intensity is determined based on at least one of a spontaneous breath rate and a spontaneous breath volume.

23. The method of claim 13, wherein the one or more drug delivery devices are automatically controlled based on the desired sedative status via a spontaneous breathing control module executable on a processor of a computing system controlling anesthesia delivery.

* * * * *